(12) United States Patent
Lu et al.

(10) Patent No.: US 6,702,456 B2
(45) Date of Patent: Mar. 9, 2004

(54) METHOD AND APPARATUS FOR EVALUATING THE PHASE CHANGING FUNCTION OF FABRIC

(75) Inventors: Ben-Cheng Lu, Taipei (TW); Lubos Hes, Liberec (CZ)

(73) Assignee: China Textile Institute, Taipei Hsien (TW)

(*) Notice: Subject to any disclaimer, the term of this patent is extended or adjusted under 35 U.S.C. 154(b) by 0 days.

(21) Appl. No.: 10/115,010

(22) Filed: Apr. 4, 2002

(65) Prior Publication Data

US 2003/0189968 A1 Oct. 9, 2003

(51) Int. Cl.[7] .............................................. G01N 25/00
(52) U.S. Cl. ....................................................... 374/45
(58) Field of Search ........................... 374/45, 102, 109, 374/29, 112, 8, 43, 44

(56) References Cited

U.S. PATENT DOCUMENTS

| | | | | |
|---|---|---|---|---|
| 2,878,669 A | * | 3/1959 | Knudson et al. ............ | 374/44 |
| 3,075,377 A | * | 1/1963 | Lang .......................... | 374/44 |
| 4,236,403 A | * | 12/1980 | Poppendiek ................ | 374/44 |
| 4,419,256 A | * | 12/1983 | Loomis ....................... | 252/62 |
| 4,647,221 A | * | 3/1987 | Szabo ......................... | 374/44 |
| 4,653,934 A | * | 3/1987 | Pursley ....................... | 374/31 |
| 5,005,985 A | * | 4/1991 | Piörkowska-Galeska et al. ............... | 374/44 |
| 5,211,476 A | * | 5/1993 | Coudroy .................... | 374/102 |
| 5,333,953 A | * | 8/1994 | Kon ............................ | 374/109 |
| 5,520,042 A | * | 5/1996 | Garritano et al. ............ | 374/46 |
| 5,622,430 A | * | 4/1997 | Pletka et al. ................. | 374/45 |
| 5,667,301 A | * | 9/1997 | Jurkowski et al. .......... | 374/43 |
| 5,940,784 A | * | 8/1999 | El-Husayni .................. | 374/43 |
| 6,183,128 B1 | * | 2/2001 | Beran et al. ................. | 374/44 |
| 6,257,761 B1 | * | 7/2001 | Chuah et al. ................ | 374/45 |
| 6,408,256 B1 | * | 6/2002 | Hittle et al. ................ | 374/178 |
| 6,536,943 B1 | * | 3/2003 | Feske ........................... | 374/8 |
| 2002/0191669 A1 | * | 12/2002 | Fan et al. .................... | 374/45 |

FOREIGN PATENT DOCUMENTS

| | | | | |
|---|---|---|---|---|
| FR | 2613488 A2 | * | 10/1988 | .................. 374/43 |
| JP | 60088360 A | * | 5/1985 | .................. 374/43 |
| JP | 61028852 A | * | 2/1986 | .................. 374/43 |

* cited by examiner

*Primary Examiner*—Diego Gutierrez
*Assistant Examiner*—Mirellys Jagan
(74) *Attorney, Agent, or Firm*—Troxell Law Office PLLC

(57) ABSTRACT

The present invention relates to a method and an apparatus for evaluating the phase changing function of fabric. First, a fabric with phase changing material to be evaluated its phase changing function is provided and positioned between a body temperature device and an environment temperature device. Then, said fabric is heated by a controller through two control means for simulating the temperature of a human body and nature environment respectively, wherein said controller is connected with said body temperature device and with said environment temperature device separately with two control signal cables for controlling temperature, and said fabric generates a body thermal signal and an environment thermal signal. A record device is provided for receiving said body thermal signal and said environment thermal signal through at least a feedback signal cables. At last, said record device records and outputs an efficient protection time (the time that fabric is heated by said controller) and a body thermal variate of said fabric for evaluating the phase changing function thereof.

10 Claims, 3 Drawing Sheets

METHOD AND APPARATUS FOR EVALUATING THE PHASE CHANGING FUNCTION OF FABRIC

FIELD OF THE INVENTION

The invention herein relates to evaluating the function of a fabric, particularly, relates to evaluating the function of fabric with phase changing material.

BACKGROUND OF THE INVENTION

The use of phase change material (PCM) in textiles is an alternative form of improving the thermal insulation of the textiles to the high volume insulation, which is the standard thermal insulation applied when using non-wovens. They can reduce drastically the textile material volume for the same insulation performance. It is also a unique way of transmitting comfort by absorbing excess heat and releasing it when needed. The way PCM work is explained by the fact, when altering phase, it displays a very large latent heat, and while doing so, it retains the energy and provides thermal insulation.

However, the problem is how to evaluate their performance, since it is dynamic heat insulation, different to the traditional heat resistance. To address this problem, this invention provides a method and an apparatus for evaluating the phase changing function of fabric.

Thus, the present invention is provided for solving the aforementioned problem, which is developed and based on the equation of:

$$\tau_P = L/q_P = L*R/(t_E - t_{PC});$$

wherein L represents the total energy for altering phase; which relates the thermal resistance of the protective of PCM (phase changing material) R and the temperature difference of the phase change $t_P$ of the PCM and the environment $t_E$ to the time of thermal protection $\tau_P$. Therefore, referring to the FIG. 3, the body thermal state of a fabric with phase changing material (also heated by an environment temperature device) to be evaluated its phase changing function is recorded as the FIG. 3, and comparing to the dot line, which indicates a fabric without phase changing material, it can be seen that the thermal variate of the fabric with PCM increases much slower than that without PCM (as the dot line shown in the FIG. 3). The time that a general material fabric (without any PCM) reaches the final heat flow ($q_{max}$) is substantially equal to that the PCM reaches the $q_P$ (about ½ $q_{max}$), and the time that PCM reaching $q_P$ takes is called efficient protection time ($\tau_P$), which is the protection level of thermal; wherein the final heat flow ($q_{max}$) will be the same for both PCM fabric and non-PCM fabric after a very long time.

SUMMARY OF THE INVENTION

This invention provides a method and an apparatus for evaluating the phase changing function of fabric. First, a fabric with phase changing material to be evaluated its phase changing function is provided and positioned between a body temperature device and an environment temperature device, and two surfaces of said fabric contact with said body temperature device and said environment temperature device respectively. Then, said fabric is heated by a controller for simulating the temperature of a human body and nature environment through two control means respectively, wherein said controller is connected with said body temperature device and said environment temperature device through two control signal cables separately for controlling temperature. Said body temperature device and said environment temperature device generate body thermal signal and environment thermal signal respectively. A record device is provided for receiving said body thermal signal and said environment thermal signal through at least a feedback signal cable. At last, said record device records and outputs the efficient protection time and the body thermal variate of said fabric for evaluating the phase changing function thereof.

BRIEF DESCRIPTION OF THE DRAWINGS

The present invention will be better understood from the following detailed description of preferred embodiments of the invention, taken in conjunction with the accompanying drawings, in which.

DESCRIPTION OF THE PREFERRED EMBODIMENTS

The following descriptions of the preferred embodiments are provided to understand the features of the present invention.

Figure 1:
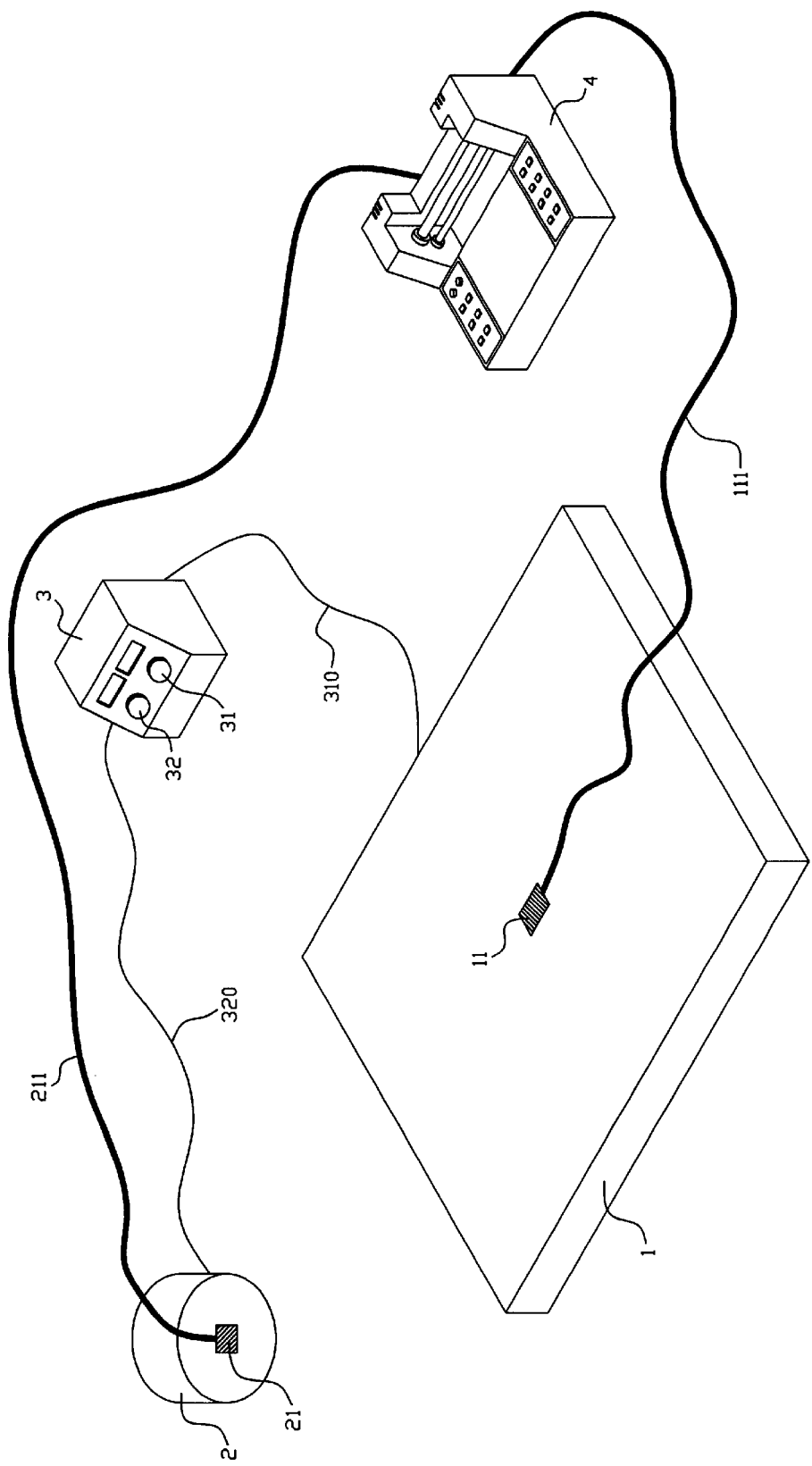
FIG. 1 and FIG. 2 are the outer diagrams of the present invention.

Referring to the FIG. 1, the present invention provides an apparatus for evaluating the phase changing function of fabric. Said apparatus comprises a body temperature device 1 for simulating the temperature of a human body and generating body thermal signal, an environment temperature device 2 for simulating the temperature of nature environment and generating environment thermal signal, a controller 3 having two control means 31 and 32 for controlling the temperature of said body temperature device 1 and said environment temperature device 2 respectively, and a record device 4 for recording and outputting the efficient protection time and the body thermal variate of a fabric 5 (as shown in the FIG. 2) for evaluating the phase changing function thereof (referring to the evaluating chart in FIG. 3). Said controller 3 connects to said body temperature device 1 and to said environment temperature device 2 separately with two control signal cable 310 and 320 for controlling temperature. In the preferred embodiment, the temperature of body temperature device 1 is controlled by said controller 3 for simulating the temperature of a human body with —50° C.~50° C. (such as the normal range of the human temperature between 25° C.~35° C.), and the temperature of said environment temperature device is controlled between 0° C.~170° C. (such as the solar heat flow with 1200 W/m²). Said record device 4 receives body thermal signal and environment thermal signal thought two feedback signal cables, such as the preferred embodiment herein 111 and 211, and then, recording and outputting the efficient protection time and the body thermal variate of said fabric 5 on a regular paper for evaluating the phase changing function thereof (referring to FIG. 3 for the evaluating chart with the output of the recording). In a preferred embodiment, said body temperature device 1 further comprises a body thermal sensor 11 for detecting the body thermal signal of first surface 51 of said fabric 5 and providing said body thermal signal to said record device 4 through the feedback signal cable 111; and said environment temperature device 2 further comprises an environment thermal sensor 21 for detecting the environment thermal signal of second surface 52 of said fabric 5 and providing said environment thermal signal to said record device 4 through the feedback signal cable 211. Furthermore, said record device 4 is a dual band device that is adapted for receiving the signal with at least 2 mV and outputting the efficient protection time and the body thermal variate of said fabric 5 on a regular paper for evaluating the phase changing function (the output as shown in the FIG. 3).

Figure 2:
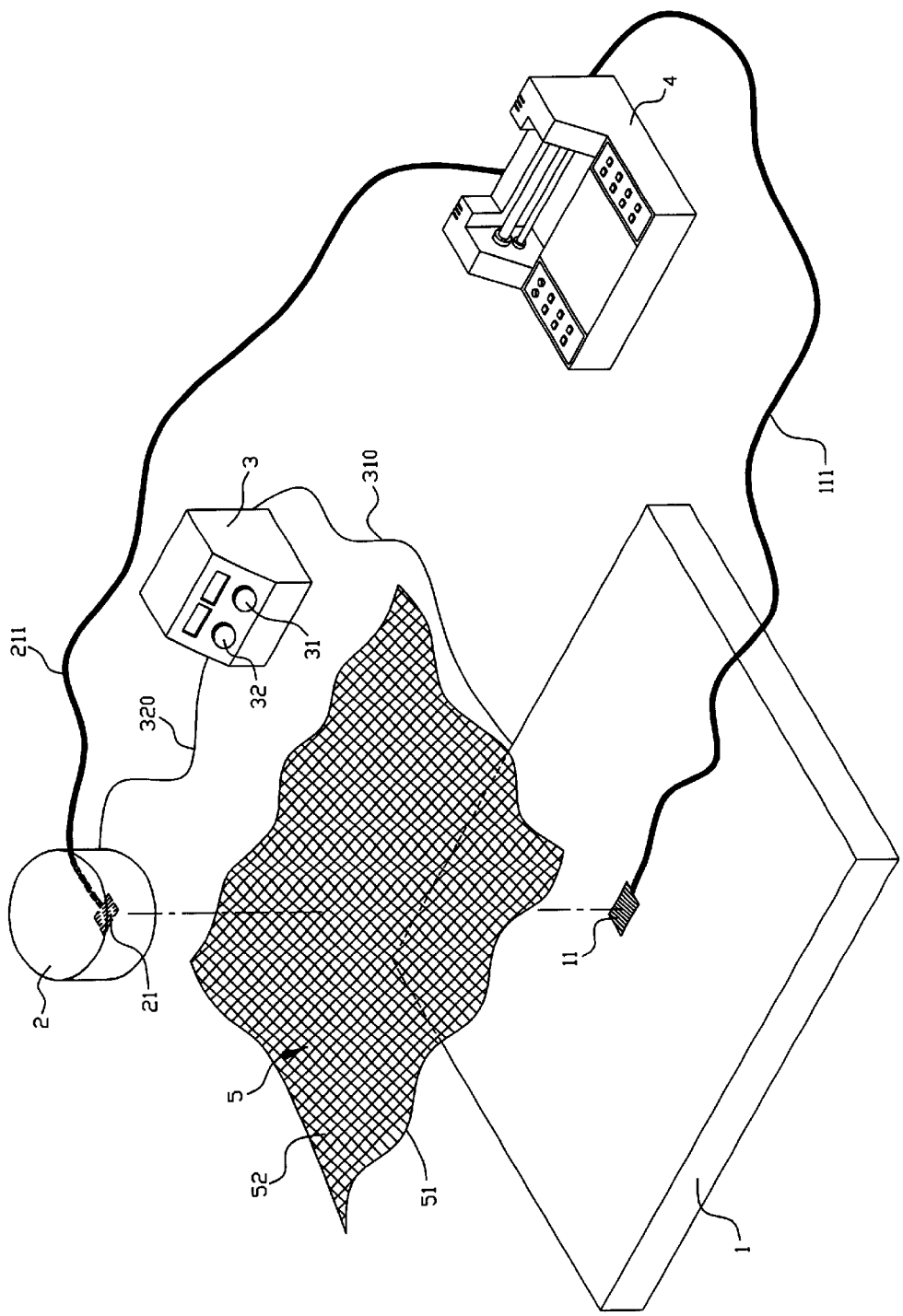
Figure 3:
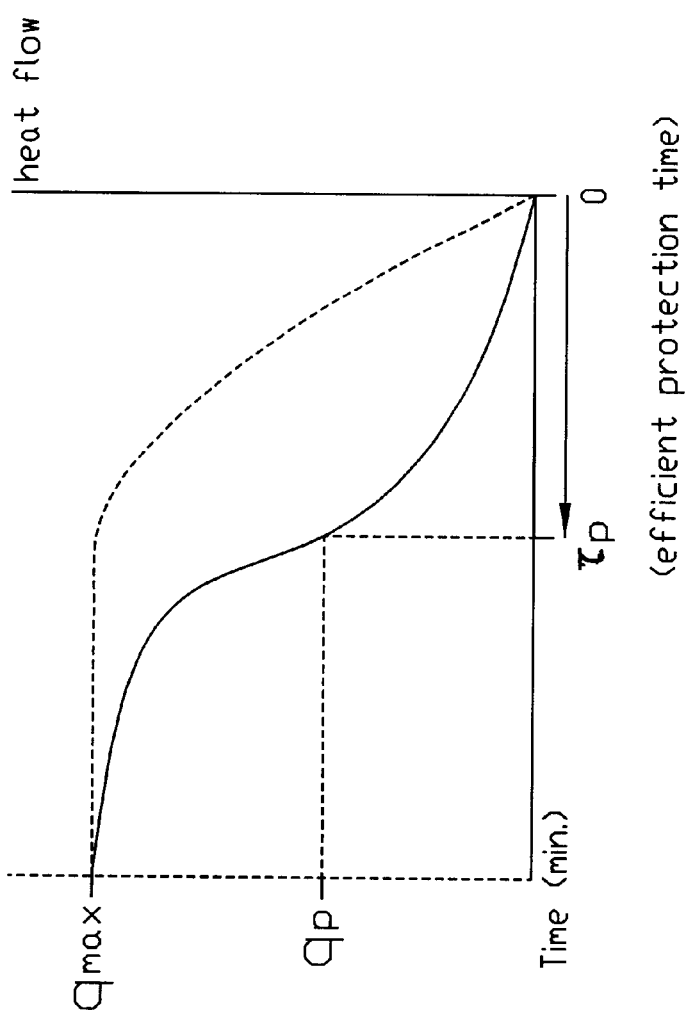
FIG. 3 is an evaluating chart in accordance with the present invention.

Next please see the FIG. 2, the present invention also provides a method for evaluating the phase changing function of fabric in accordance with the aforementioned apparatus. The method comprises the steps of: providing a fabric 5 for evaluating the phase changing function thereof; providing a body temperature device 1, an environment temperature device 2, a controller 3, and a record device 4; putting said fabric 5 on said body temperature device 1, and its first surface 51 is contacting with the body temperature device 1; and then, putting said environment device 2 on said fabric 5, and its second surface 52 is contacting with the environment device 2. Thus, the fabric 5 with phase changing material to be evaluated its phase changing function is positioned between the body temperature device 1 and the environment temperature device 2, and contacted with them. Then, said fabric 5 is heated by the controller 3 through two control means 31 and 32, wherein said controller 3 is connected to said body temperature device 1 and to said environment temperature device 2 separately with two control signal cables 310 and 320 for controlling and simulating the temperature of a human body and nature environment respectively on both surfaces 51 and 52 of said fabric 5. Said body temperature device 1 and said environment temperature device 2 generate body thermal signal and environment thermal signal respectively in accordance with the heating process; wherein said body temperature device 1 further comprises a body thermal sensor 11 for detecting the body thermal signal of first surface 51 of said fabric 5, and said environment temperature device 2 further comprises an environment thermal sensor 21 for detecting the environment thermal signal of second surface 52 of said fabric 5. In the preferred embodiment, the temperature of body temperature device 1 is controlled by said controller 3 for simulating the temperature of a human body within −50° C.~50° C. (such as the normal range of the human temperature between 25° C.~35° C.), and the temperature of said environment temperature device is controlled between 0° C.~170° C. (such as the solar heat flow with 1200 W/m$^2$). The record device 4 is provided for receiving said body thermal signal and said environment thermal signal through at least a signal cable, in the preferred embodiment herein 111 and 211. Said body temperature device 1 further comprises a body thermal sensor 11 for detecting the body thermal signal of first surface 51 of said fabric 5 and providing said body thermal signal to said record device 4 through the feedback signal cable 111; and said environment temperature device 2 further comprises an environment thermal sensor 21 for detecting the environment thermal signal of second surface 52 of said fabric 5 and providing said environment thermal signal to said record device 4 through the feedback signal cable 211. At last, said record device 4, after receiving said body and environment thermal signals, records and outputs an efficient protection time (the incremental heated time that fabric having phase changing material) and a body thermal variate of said fabric for evaluating the phase changing function thereof (referring to the FIG. 3 for the evaluating chart with the output of the recording). In the preferred embodiment, said record device 4 is a dual band device adapted for receiving the signal with at least 2 mV and outputting the efficient protection time and the body thermal variate of said fabric 5 on a regular paper for evaluating the phase changing function thereof (the output as shown in the FIG. 3).

The invention herein is developed and based on the equation of:

$$\tau_P = L/q_P = L*R/(t_E - t_{PC});$$

wherein L represents the total energy for altering phase; which relates the thermal resistance of the protective of PCM (phase changing material) R and the temperature difference of the phase change $t_{PC}$ of the PCM and the environment $t_E$ to the time of thermal protection $\tau_P$. Therefore, referring to the FIG. 3, the body thermal variate of a fabric (also heated by an environment temperature device) with phase changing material to be evaluated its phase changing function is recorded as the FIG. 3, and comparing to the dot line, which indicates a fabric without phase changing material, it can be seen that the thermal of the fabric with PCM increases much slower than that without PCM (as the dot line shown in the FIG. 3). The time that a general material fabric (without any PCM) reaches the final heat flow ($q_{max}$) is substantially equal to the PCM reaches the $q_P$ (about ½ $q_{max}$), and the time that PCM reaching $q_P$ takes is called efficient protection time ($\tau_P$), which is the protection level of thermal; wherein the final heat flow ($q_{max}$) will be the same for both PCM fabric and non-PCM fabric after a very long time. Therefore, the present invention is used for evaluating the phase changing function of fabric.

The present invention may be embodied in other specific forms without departing from the spirit of the essential attributes thereof; therefore, the illustrated embodiment should be considered in all respects as illustrative and not restrictive, reference being made to the appended claims rather than to the foregoing description to indicate the scope of the invention.

What is claimed is:

1. An apparatus for evaluating a phase changing function of a fabric comprising:
    a) one body temperature device simulating a temperature of a human body and generating a body thermal signal, the body temperature device contacting a first side of the fabric;
    b) one environment temperature device simulating a temperature of a natural environment and generating an environment thermal signal, the environment temperature device contacting a second side of the fabric;
    c) a controller having:
        i) a first control device electrically connected to the body temperature device; and
        ii) a second control device electrically connected to the environment temperature device; and
    d) a record device electrically connected to the body temperature device and the environment temperature device, the record device receiving the body thermal signal from the body temperature device and the environment thermal signal from the environment temperature device, and recording and outputting an efficient protection time and a body thermal variate of the fabric.

2. The apparatus for evaluating the phase changing function of the fabric according to claim 1, wherein the body temperature device has a body thermal sensor and the environment temperature device has an environment thermal sensor.

3. The apparatus for evaluating the phase changing function of a fabric according to claim 1, wherein the record device is a dual band device receiving a signal with at least 2 mV.

4. The apparatus for evaluating the phase changing function of the fabric according to claim 1, wherein the body temperature device simulates human body temperatures between minus 50° C. and plus 50° C.

5. The apparatus for evaluating the phase changing function of the fabric according to claim 1, wherein the environment temperature device simulates natural environment temperatures between 0° C. and 170° C.

6. A method for evaluating a phase changing function of a fabric comprising the steps of:
 a) selecting the fabric for evaluating the phase changing function thereof;
 b) positioning a first side of the fabric in contact with one body temperature device;
 c) positioning one environment temperature device in contact with a second side of the fabric;
 d) heating the fabric with the body temperature device and the environment temperature device that are controlled by two control devices of a controller;
 e) generating a body thermal signal with the body temperature device and an environmental thermal signal with the environment temperature device;
 f) receiving the body thermal signal and the environment thermal signal with a record device; and
 g) recording and outputting an efficient protection time and a body thermal variate of the fabric being evaluated.

7. The method for evaluating the phase changing function of the fabric, of claim 6, wherein the generating step e, is carried out using a body thermal sensor connected to the body temperature device to produce the body thermal signal and an environment thermal sensor connected to the environment temperature device to produce the environmental thermal signal.

8. The method for evaluating the phase changing function of the fabric, of claim 6, wherein the receiving step f, carried out by a dual band record device receiving a signal with at least 2 mV.

9. The method for evaluating the phase changing function of the fabric, of claim 6, wherein the heating step d, exposes the fabric to human body temperatures between minus 50° C. and plus 50° C.

10. The for evaluating the phase changing function of the fabric, of claim 6, wherein the heating step d, exposes the fabric to natural environment temperatures between 0° C. and 170° C.

* * * * *